United States Patent [19]
Coe

[11] Patent Number: 5,207,699
[45] Date of Patent: May 4, 1993

[54] LANCET HANDLING AND DISPOSAL ASSEMBLY

[76] Inventor: Frederick L. Coe, 526 Alameda Padre Serra, Santa Barbara, Calif. 93103

[21] Appl. No.: 789,762

[22] Filed: Nov. 8, 1991

Related U.S. Application Data

[63] Continuation of Ser. No. 684,442, Apr. 11, 1991, abandoned, which is a continuation of Ser. No. 428,634, Oct. 30, 1989, abandoned.

[51] Int. Cl.$^5$ .............................................. A61B 17/32
[52] U.S. Cl. .................................. 606/182; 128/919; 604/192; 604/263
[58] Field of Search ............... 128/917, 919; 606/181, 606/185, 182, 183, 186; 604/192, 263, 193, 199, 110

[56]           References Cited
        U.S. PATENT DOCUMENTS

| | | | |
|---|---|---|---|
| 2,857,912 | 10/1958 | Feinstone et al. | 604/192 |
| 4,230,118 | 10/1980 | Holman et al. | |
| 4,452,243 | 6/1984 | Leopoldi et al. | |
| 4,577,630 | 3/1986 | Nitzsche et al. | 606/182 |
| 4,635,633 | 1/1987 | Hufnagle | 606/181 |
| 4,738,261 | 4/1988 | Enstrom | 606/185 X |
| 4,747,837 | 5/1988 | Hauck | 604/198 |
| 4,869,249 | 9/1989 | Crossman et al. | 606/182 |
| 4,874,384 | 10/1989 | Nunez | 128/919 X |
| 4,889,117 | 12/1989 | Stevens | 606/185 X |
| 4,932,940 | 6/1990 | Walker et al. | 604/263 |
| 4,973,315 | 11/1990 | Sincock | 604/263 X |

FOREIGN PATENT DOCUMENTS 2622515  12/1976  Fed. Rep. of Germany ...... 604/192

OTHER PUBLICATIONS

Morbidity and Mortality Weekly Report, Jun. 24, 1988, vol. 37 No. 24 Publ. by the Massachusetts Medical Society pp. 377-388.

Primary Examiner—Michael H. Thaler
Attorney, Agent, or Firm—Michael G. Petit

[57]              ABSTRACT

A lancet extraction and handling assembly adapted for protectively covering and removing a lancet from an automatic lancet device. In all preferred embodiments the lancet has a slotted hub portion. In one preferred embodiment, the extractor has a hollow, substantially cylindrical covering portion which slides over the lancet hub to protectively cover the sharp tip. The covering portion of the lancet extractor has a flexible tab on its inner surface mated to the slot in the hub of the lancet which permits easy insertion of the lancet into the extractor. When the extractor is positioned over the lancet, the extractor tab engages the lancet slot to resist undesired removal of the lancet from the extractor. Pilot means may be provided to guide the extractor over the lancet to facilitate proper registration of the extractor tab with the lancet slot. Alternatively, a visual indicator may also be provided to facilitate registration of the extractor tab with the lancet slot when the extractor is slid over the lancet for removal.

4 Claims, 2 Drawing Sheets

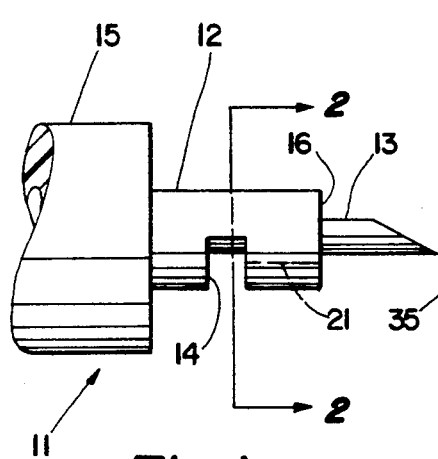
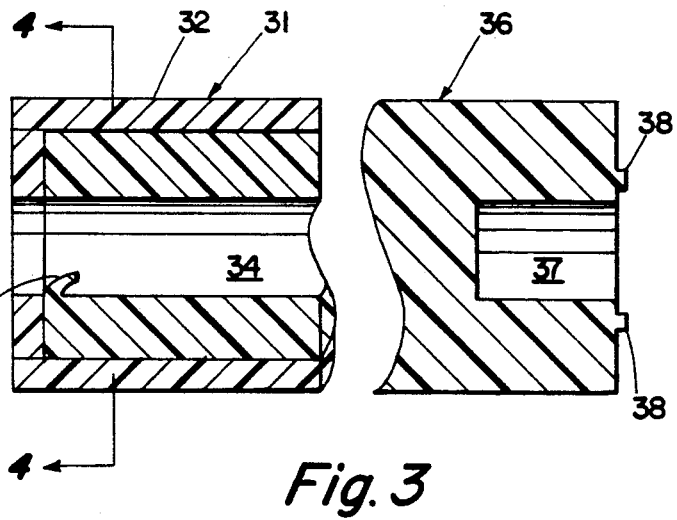
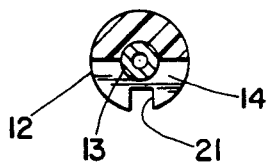
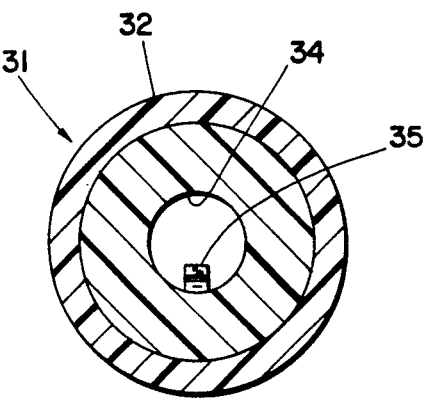
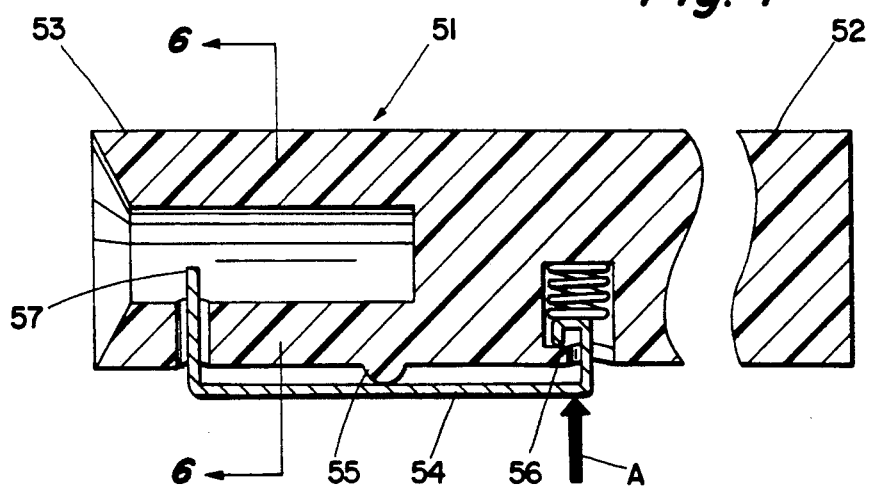

LANCET HANDLING AND DISPOSAL ASSEMBLY

This is a continuation of application Ser. No. 07/684,442, filed Apr. 11, 1991, abandoned which is a continuation of Ser. No. 07/428,634 filed Oct. 30, 1989 abandoned.

BACKGROUND OF THE INVENTION

1. Field of the Invention

This invention relates to a blood lancet extraction and disposal assembly for use with an automatic lancet device of the type commonly used for taking skin capillary blood samples, and more specifically, it relates to an assembly wherein means are provided to resist undesired lancet puncture wounds during and after removal of the disposable lancet from the automatic lancet device.

2. Description of the Prior Art

Blood lancets are used for drawing a small amount of blood, e.g. for diagnostic purposes, by a short prick, preferably into the ball of the finger. As a rule, one uses sterile disposable lancets to avoid the danger of infection. Blood lancets which are stamped out of a thin metal sheet are common.

Another kind of blood lancet consists of a hub (or handle) injection molded of plastic in one piece with an integrally molded steel tip. The tip of these blood lancets is relatively blunt because on the one hand, a fine tip is difficult to produce by injection molding and, on the other hand, a fine tip easily breaks off during transport and storage. To make and protect a fine tip, the tip is surrounded by a plastic protective cap which is extruded in one piece with retaining attachment points and is twisted off before use of the lancet.

Holman et al, in U.S. Pat. No. 4,230,118, describe an automatic lancet device for use in pricking a patient's skin to yield a blood sample. The device comprises an arm, one end of which arm is pivotally mounted in a housing and its other, or outer, end protruding from the housing through an arcuate slot in the housing, the outer end of the arm being formed into a carrier which will hold a replaceable mountable lancet with its point projecting tangentially to the pivotal arc of the arm. The arm is spring biased in the angular direction corresponding to the direction in which the lancet points and can be held retracted against the spring means by a latch in the housing. When the latch is released, the arm springs forward causing the lancet attached thereto to strike a detachable finger rest. The detachable finger rest which is mounted in the housing, includes a ring for resting on the patient's skin so that the sharp lancet tip projects through the ring for pricking.

Leopoldi et al, in U.S. Pat. No. 4,452,243, describe another automatic blood lancet device which includes a fingertip element to be held by a user and a hinged striker element pivotally mounted on the device and spring-actuated to drive a lancet secured on the striker into the fleshy fingertip. A thumb piece on the striker is provided to draw the striker back into a cocked position. This device is intended for use with a lancet that has a twist-off or tear-away protective cap for maintaining the sanitary condition of the lancet until it is to be used. The striker element is flexible and the finger grip element is provided with an upstanding projection on the top surface, which the striker contacts and about which the striker flexes when it is spring-actuated downwardly about its pivot, whereby the puncturing element is thrust downwardly below the bottom surface of the finger grip element to puncture the flesh and then be retracted upwardly when it rebounds to dispose the puncture element substantially above such bottom surface in a withdrawn position.

Both the Holman and Leopoldi inventions described above provide a hinged striker element of flexible construction for driving a sharp puncturing device such as a lancet into the fleshy fingertip pad and which is integrally associated with a mounting element that includes a generally flat surface member on which the striker element is pivotally secured for hinged movement. The lancet, when used in either device, must be removed manually and without the protection of a safety cap.

In 1983, the Center for Disease Control published a document entitled "Guideline for Isolation Precautions in Hospitals" that contained a section entitled "Blood and Body Fluid Precautions." The recommendations in this section called for precautions in handling blood and body fluids when a patient was known or suspected to be infected with blood borne pathogens. Partly in response to the serious risk to hospital workers exposed to patients infected with the HIV virus, CDC published a more detailed guideline entitled, "Recommendations for Prevention of HIV Transmission in Health Care Settings" in August, 1987. In contrast to the 1983 document, the 1987 document recommended that blood and body fluid precautions be consistently used for all patients regardless of their blood-borne infection status. This extension of blood and body fluid precautions to all patients is referred to as "universal blood and body fluid precautions" or simply "universal precautions." Under universal precautions, blood and certain body fluids of all patients are considered potentially infectious for human immune deficiency virus (HIV), hepatitis B virus (HBV), and other blood-borne pathogens.

Universal precautions are intended to prevent contact, and exposure of health care workers to blood-borne pathogens. In addition, immunization with HBV vaccine is recommended as an important adjunct to universal precautions for health care workers who have exposures to blood.

Much attention has gone into protecting workers from needle stick injuries. Such accidental needle stick injuries have even resulted in transmission of the HIV virus to the workers. Accidental needle sticks with needles which have had patient contact commonly result in transmission of viral hepatitis. Other diseases which may be transmitted in like fashion are herpes, streptococcus, staphylococcus, tuberculosis, malaria and syphilis.

Many innovative devices have been developed to address the problem of preventing accidental needle-stick injuries. U.S. Pat. No. 4,356,822 discloses a syringe assembly wherein an outer tubular member is adapted to control the depth of needle penetration into the patient. Smith, Jr., in U.S. Pat. No. 4,643,722 describes a slotted needle sheath hinged to the hub of the needle. Luther, in U.S. Pat. No. 4,747,836 describes another needle guard which is a slotted tube which slips over the needle.

In spite of the foregoing work with needles, nothing has been done to protect hospital workers or other health care providers from accidental sticks from a lancet. In general, in regard to lancets, existing systems provide a cap member having a closed end wall positioned over the lancet which is attached to the hub or base portion of the lancet. The cap is removed by breaking it away from the hub portion at breakaway points which are molded into the hub. Normally, the lancet may be disposed of by merely discarding without capping inasmuch as the cap is provided to protect the sharp point prior to use and is not generally suitable for recapping the lancet. Rigid boxes ("sharps" containers) having suitable openings for receipt of used lancets are commonly employed.

There remains a significant need for an extraction and closure member for lancets which will effectively cover the lancet tip, maintain sterility, if necessary, and minimize the risk of accidental puncture wounds both during and after removal of the lancet from an automatic lancet device.

SUMMARY OF THE INVENTION

In the present invention, an extraction member, which is adapted to effectively lock to and protectively cover the sharp tip of a disposable lancet, is provided with a tab which mates with a slot on the hub of the lancet to effect securement of the lancet within the extractor for removal from an automatic lancet device.

Means may be provided to permit manual indexing or registration of the closure so as to orient the slot in the lancet hub with the tab in the extractor more readily. Also, pilot entry means may be provided to facilitate insertion of the extractor onto the lancet hub so that the extractor tab and lancet slot are in registration. The extractor is preferably substantially rigid and may advantageously be molded from the same plastic resinous material as the lancet hub.

It is an object of the present invention to provide a lancet extraction assembly which will effectively minimize hazards to medical personnel resulting from accidental lancet punctures.

It is yet another object of the present invention to provide such an assembly which will be simple to use and economical to adopt.

It is a further object of the present invention to provide for disposal of used lancets in such a fashion as to minimize risk to housekeeping personnel.

These objects of the present invention will be more fully understood from the following description of the invention with reference to the illustrations appended hereto.

BRIEF DESCRIPTION OF THE DRAWINGS

FIG. 1 is a cross-section side elevation of the first preferred embodiment of the improved lancet of the present invention.

FIG. 2 is a cross-sectional end elevation of the improved lancet of the present invention, taken along line 2—2 of FIG. 1.

FIG. 3 is a cross-sectional side elevation of the first preferred embodiment of the lancet extractor of the present invention.

FIG. 4 is a cross-sectional end elevation of the lancet extractor of the present invention taken along line 4—4 of FIG. 3.

FIG. 5 is a cross-sectional side elevation of a second preferred embodiment of a lancet extractor for use with the improved lancet of FIG. 1.

DESCRIPTION OF THE PREFERRED EMBODIMENT

Figure 6:
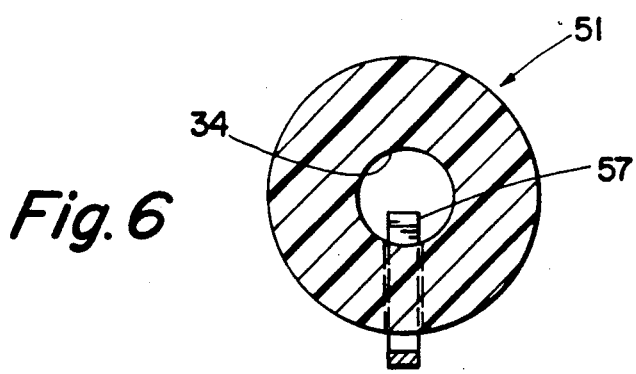
FIG. 6 is a cross-sectional end elevation of the lancet extractor of FIG. 5 taken along line 6—6.

Turning now to FIG. 1, the outer end of the pivoting arm (15) of an automatic lancet device (not shown) is shown with a blood lancet (11) in position for use. The blood lancet (11) consists of a slotted hub (12) which forms the proximal end of the blood lancet and a sharp, usually stainless or surgical steel, tip (13) affixed to the distal end. The sharp tip (13) can be insertion molded into the plastic hub (12) which has a retrieval or removal slot (14) cut therein. The hub (12) of the lancet is dimensioned to fit into a mating hole in the pivotal arm (15) of an automatic lancet device of the type well known in the art (see, for example, U.S. Pat. No. 4,230,118 to Holman, et al, or U.S. Pat. No. 4,856,515 to Turner, et al.). The lancet hub may have a registration key (21) (FIG. 2) between the slot (14) and the tip (16), as shown in FIG. 2, to enable the proper orientation between the locking tab (35) in the protective cap (31) and the removal slot (14) in the hub (12).

Referring now to FIG. 3, the protective cap (31) is a substantially cylindrical member (32) with two cavities therein, both of which cavities open to the outside. A non-releasing cavity (34) receives and protectively envelopes the sharp tip (13) of the lancet (11) after the sharp tip (13) has been used to puncture the skin and is contaminated with blood. The non-releasing cavity has a cross-sectional profile (FIG. 4) which mates with the cross-sectional profile of the blood lancet (12) (FIG. 2). A flexible plastic looking tab (35) is disposed within the non-releasing cavity to lockingly engage the removal slot (14) of the lancet (11) when the non-releasing cavity (34) in the protective cap is slid over the lancet hub (12). Once the locking tab (35) engages the removal slot (14), the protective cap (31) and the blood (11) lancet cannot be separated. They are locked together with the sharp lancet tip (13) completely enclosed within the non-releasing cavity. The protective cap/lancet may then be safely removed from the pivotal arm (15) of the automatic lancet and disposed of without danger to refuse handlers.

The protective cap (31) also has a releasing cavity (37) for receiving and protectively enclosing the sharp tip (13) of the blood lancet (11) prior to pricking the skin. Breakaway contact points (38) on the surface of the protective cap (31) adjacent to the releasing cavity (37) enable the protective cap (31) to be removed from the blood lancet (11) with a simple twist once the lancet hub (12) has been seated within the pivotal arm (15) of an automatic lancet. The releasing cavity (37) in the end of the protective cap thereby serves as a releasable housing for the lancet tip (13) until the lancet (11) is ready to be used to prick the skin. The non-releasable cavity (34) in the other end of the protective cap (31) serves as a non-releasable housing to envelop and protectively enclose the blood-contaminated lancet tip (13) after use.

Figure 7:
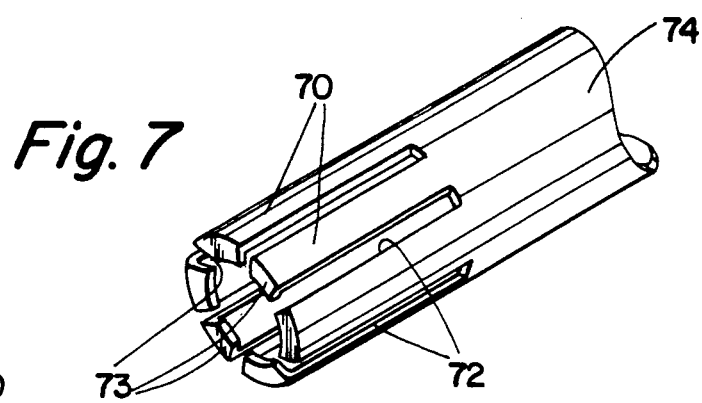
FIG. 7 is a somewhat side perspective elevation of a third preferred embodiment of a lancet extractor for use with the improved lancet of FIG. 1.
Figure 8:
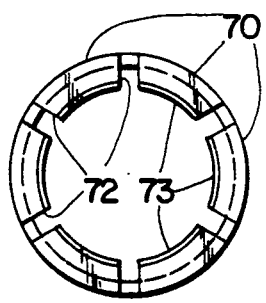
FIG. 8 is an end elevation of the lancet exterior of FIG. 7.

A third embodiment of a disposable lancet extractor and protective capping device is shown in FIG. 7. In this embodiment, flexible fingerlike projections (70) are fixed firmly to a handle end (74). The other end of each projection has a beveled tab (73) which is proportioned to mate with the slot in a lancet hub (FIG. 1 (14)). As the extractor is pushed over the lancet to protectively cover the lancet's sharp tip, the beveled tab causes the fingerlike projections to splay outward to surround and accommodate the lancet. The spacing of the fingerlike projections on the extractor is designed to enable one or more of the tabs (73) in the end of the fingerlike projection to align with the slot in the lancet hub. The restorative elastic force exerted by the splayed fingerlike projection forces the tab (73) into the slot (14) (FIG. 1) thereby locking the lancet protectively within the enclosure defined by the array of fingerlike projections. This embodiment requires no means for alignment of the locking tab with the hub slot inasmuch as the number of fingerlike projections and tab size can be varied to assure alignment of at last one tab with the slot. In addition, this embodiment, like the first two, can be integrally molded to the lancet with suitable breakaway points so that it can be used both as a protective lancet tip cover before use and a protective disposable tip cap after use.

Figure 9:
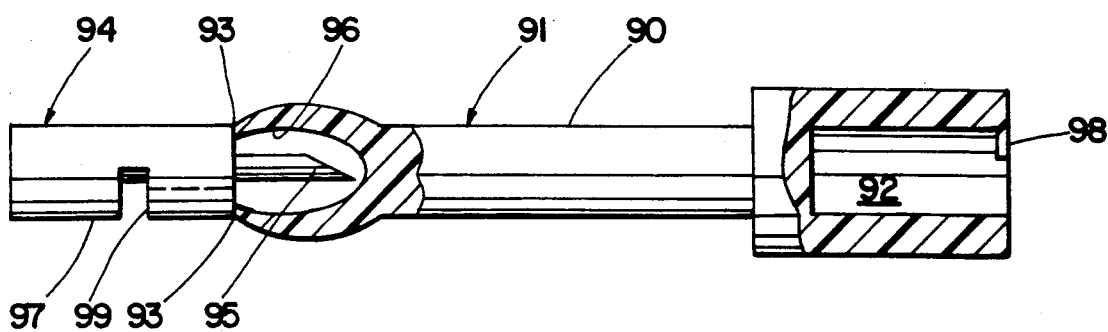
FIG. 9 is a perspective view of a lancet extractor integrally molded to a lancet to protect the lancet tip before use.

FIG. 9 shows how a lancet extractor and handling device of the present invention may be integrally molded to a lancet (94). The extractor (91) has a handle portion (90) and an extractor cavity (92). On the end of the handle opposite the extractor cavity, there is a second cavity (96) protectively covering the sharp tip (95) of the lancet (94). The handle portion of the extractor is attached to the hub of the lancet (97) by breakaway points (93). In practice, the lancet is inserted into an automatic lancet device. The sterile lancet tip is then bared for use by breaking away the handle portion at the breakaway points by gentle twisting. After use, the lancet is inserted (point first) into the extractor cavity until the extractor tab (98) engages the slot (99) in the lancet hub thereby locking the sharp lancet tip protectively within the extractor cavity for safe handling and disposal.

It is readily appreciated by those of ordinary skill in the art that many designs are possible which will facilitate either a locking or releasable locking union between a lancet and a lancet cover and serve as a safe means for extracting a lancet from an automatic lancet device. For example, an extractor may be designed with barb-like projections on the interior surface of the cylindrical cover portion in which the sharp tips of the projections point in the same direction as the top of the lancet. Such an extractor will slide easily over the lancet to cover it but will not be removable.

What I claim is:

1. A blood lancet assembly comprising, in combination, a blood lancet and a protective cap; said blood lancet having a sharp tip suitable for puncturing the skin and a substantially cylindrical hub dimensioned to removably attach to the pivotal arm of an automatic lancet device, said protective cap further comprising:
   (a) a first cavity for receiving and protectively enveloping the sharp tip of said blood lancet prior to use of said blood lancet;
   (b) means for releasably securing said lancet to said cap when said sharp tip is protectively enclosed within said first cavity;
   (c) a second cavity for receiving and protectively enveloping the sharp tip of said blood lancet after said blood lancet has been used to puncture the skin; and
   (d) means within said second cavity for non-releasably securing said lancet to said cap when the sharp tip of said lancet is enclosed within said second cavity.

2. The blood lancet assemble of claim 1 wherein said hub has a removal slot comprising an indentation in the outer surface thereof.

3. The blood lancet assemble of claim 2 wherein said means for non-releasably securing said lancet to said cap comprises a locking tab projecting inwardly from the wall of said second cavity dimensioned to lockingly engage said removal slot in said lancet hub when the sharp tip of said lancet is enclosed within said second cavity.

4. The blood lancet assemble of claim 1 or 3 wherein said means for releasably securing said lancet to said cap comprises a breakaway connection attaching said protective cap to said blood lancet when said sharp tip is protectively enclosed within said first cavity.

* * * * *